United States Patent
Yu et al.

(10) Patent No.: US 11,651,488 B2
(45) Date of Patent: May 16, 2023

(54) DEVICES AND METHODS FOR DETERMINING A DISEASE STATE BASED TOTAL LENS FLUORESCENCE

(71) Applicant: YuScan USA, LLC, Norcross, GA (US)

(72) Inventors: Nai-Teng Yu, Marietta, GA (US); Mark A. Samuels, Sugar Hill, GA (US); Rong-Chun Yu, Diamond Bar, CA (US)

(73) Assignee: YUSCAN USA, LLC, Norcross, GA (US)

( * ) Notice: Subject to any disclaimer, the term of this patent is extended or adjusted under 35 U.S.C. 154(b) by 286 days.

(21) Appl. No.: 17/039,087

(22) Filed: Sep. 30, 2020

(65) Prior Publication Data

US 2021/0097683 A1 Apr. 1, 2021

Related U.S. Application Data

(60) Provisional application No. 62/911,746, filed on Oct. 7, 2019, provisional application No. 62/909,233, filed (Continued)

(51) Int. Cl.
*G06T 7/00* (2017.01)
*A61B 5/00* (2006.01)

(52) U.S. Cl.
CPC .......... *G06T 7/0012* (2013.01); *A61B 5/0013* (2013.01); *A61B 5/0059* (2013.01);
(Continued)

(58) Field of Classification Search
None
See application file for complete search history.

(56) References Cited

U.S. PATENT DOCUMENTS

| 8,989,848 B2 | 3/2015 | Rorabaugh et al. |
| 2010/0208207 A1* | 8/2010 | Connell II ........... G06V 40/193 |
| | | 351/210 |

(Continued)

OTHER PUBLICATIONS

International Preliminary Report on Patentability received for related PCT Application No. PCT/US2020/053542 dated Apr. 14, 2022 (8 pages).

*Primary Examiner* — Vu Le
*Assistant Examiner* — Courtney Joan Nelson
(74) *Attorney, Agent, or Firm* — The Small Patent Law Group LLC; Josef L. Hoffmann

(57) ABSTRACT

A device is provided that may include an illuminator operable to interrogate at least a lens of an eye. The illuminator may include at least one light source and a lens positioned with respect to the light source to produce interrogating radiation. The device also may include a detector operable to image the total autofluorescence response of the lens of the eye as viewable through a pupil of the eye, the detector comprising an image sensor. The device can also include a controller operable to control operation of the illuminator and the detector. The controller may interrogate at least the lens of the eye by activating the illuminator for a select time, obtain at least one image of the total autofluorescence response of the lens at the detector during or immediately subsequent to the select time, and transmit the at least one image to a remote device.

16 Claims, 6 Drawing Sheets

Related U.S. Application Data on Oct. 2, 2019, provisional application No. 62/908,934, filed on Oct. 1, 2019.

(52) U.S. Cl.
CPC ...... *A61B 5/48* (2013.01); *G06T 2207/10064* (2013.01); *G06T 2207/30041* (2013.01)

(56) References Cited

U.S. PATENT DOCUMENTS

| | | | |
|---|---|---|---|
| 2012/0203086 A1* | 8/2012 | Rorabaugh | A61B 3/1173 600/321 |
| 2013/0053700 A1 | 2/2013 | Ignotz et al. | |
| 2014/0176905 A1* | 6/2014 | Nakano | A61B 3/102 351/206 |

* cited by examiner

DEVICES AND METHODS FOR DETERMINING A DISEASE STATE BASED TOTAL LENS FLUORESCENCE

CROSS REFERENCE

This application claims the benefit of and priority to U.S. Provisional Patent Application Ser. No. 62/908,934, filed Oct. 1, 2019, entitled, "METHODS AND SYSTEMS FOR DETERMINING A DISEASE STATE BASED ON AUTO-FLUORESCENCE", U.S. Provisional Patent Application Ser. No. 62/909,233, filed Oct. 2, 2019, entitled, "DEVICES AND METHODS FOR DETERMINING A DISEASE STATE BASED ON LENS FLUORESCENCE", and U.S. Provisional Patent Application Ser. No. 62/911,746, filed Oct. 7, 2019, entitled "DEVICES AND METHODS FOR DETERMINING A DISEASE STATE BASED ON LENS FLUORESCENCE". The disclosures of these related applications are incorporated by reference in their entirety into this present application.

BACKGROUND

Embodiments herein generally relate to devices, methods, and systems for determining a disease state based on total lens fluorescence.

Early detection of a chronic or potentially chronic disease state of a patient can be of paramount importance in managing the long-term well-being of the patient. For example, diabetes mellitus is a chronic debilitating disease that impairs the ability of the body to metabolize sugar, resulting in inadequate control of glucose that, if left untreated, can lead to a variety of health complications. Once diagnosed, the diabetic must be under a treatment regimen for life.

Diabetes was the seventh leading cause of death in the United States in 2010 based on the 234,051 death certificates in which 69,071 diabetes was listed as the underlying cause of death. Diabetes may be under reported as a cause of death. Studies have found that only about 35% to 40% of people with diabetes who died had diabetes listed anywhere on the death certificate and about 10% to 15% had it listed as the underlying cause of death.

Before people develop type 2 diabetes, they almost always have "pre-diabetes"—average blood glucose levels that are higher than normal but not yet high enough to be diagnosed as diabetes. Doctors sometimes refer to pre-diabetes as impaired glucose tolerance (IGT) or impaired fasting glucose (IFG), depending on what test was used when it was detected. This condition indicates a higher risk for developing type 2 diabetes and cardiovascular disease. In some cases, it is possible to prevent or slow the development of type 2 diabetes in pre-diabetes patients with changes in diet and lifestyle.

Current methods for diabetes, IGT, and IGF screening utilizing random "finger stick" glucose (no fasting) are no longer recommended by healthcare authorities because the random nature of the test lacks sensitivity and specificity. Due to the pain of a finger stick or blood draw and the poor performance of these tests, many individuals avoid current diabetes screening programs. Also, in the U.S. the current rules (Clinical Laboratory Improvement Act of 88, CLIA 88) regulating blood testing in physicians' offices or alternate sites make this type of screening difficult to carry out. Glucose urine testing, the most common method of diabetes screening, has even lower test sensitivity and specificity. Due to the insufficiency of current methods for diabetes, IGT, and IGF screening, many diabetics go undetected for many years and many pre-diabetes patients progress to type 2 diabetes. In fact, a large percentage of diabetics who are detected using current methods in the United States (600,000 per year) have late-stage complications due to type 2 diabetes. Accordingly, it is desirable to provide convenient, painless, accurate, and non-invasive methods and systems for that enable detection of a chronic or potentially chronic disease state of a patient.

BRIEF DESCRIPTION

In one or more embodiments, a device is provided that may include an illuminator operable to interrogate at least a lens of an eye. The illuminator may include at least one light source and a lens positioned with respect to the light source to produce interrogating radiation. The at least one light source may be fixed relative to an eye aperture disposed in a housing of the device. The device also may include a detector operable to image the total autofluorescence response of the lens of the eye as viewable through a pupil of the eye, the detector comprising an image sensor. The device can also include a controller operable to control operation of the illuminator and the detector, wherein the controller includes an input to receive an instruction to perform an action, one or more processors, and a memory storing program instructions accessible by the one or more processors. Responsive to execution of the program instructions, the one or more processors may interrogate at least the lens of the eye by activating the illuminator for a select time, obtain at least one image of the total autofluorescence response of the lens at the detector during or immediately subsequent to the select time, and transmit the at least one image to a remote device.

In one or more embodiments, a method is provided that can include interrogating at least a lens of an eye by activating an illuminator for a select time. The illuminator may include at least one light source and a lens positioned with respect to the light source to produce interrogating radiation, and the at least one light source is fixed relative to an eye aperture disposed in a housing of the device. The method may also include obtaining at least one image of the total autofluorescence response of the lens of the eye as viewable through a pupil of the eye from a detector. Specifically, the detector may be operable to image the total autofluorescence response of the lens, the detector comprising an image sensor. The method may also include transmitting the at least one image to a remote electronic device.

In one or more embodiments, a method may be provided that includes analyzing a plurality of candidate images of the total autofluorescence response of the lens of the eye as viewable through a pupil of the eye. Analyzing each image of the plurality of candidate images may include analyzing the image to determine a symmetry value and a definition value of a pupil spot of a pupil, analyzing the symmetry value and the definition value of the pupil to determine at least one confirmed image, discerning a median location of a peak of the at least one confirmed image, performing an average of an area of the median location of the peak of the at least one confirmed image, and determining a total lens autofluorescence index based on the average of the area of the median location of the peak of the at least one confirmed image.

In one or more embodiments, a computer program product is provided that includes a non-signal computer readable storage medium comprising computer executable code. The computer executable code may interrogate at least a lens of an eye by activating an illuminator for a select time. The illuminator may include an array of at least three sources that are spaced about to a central point, each of the at least three sources fixed relative to an eye aperture disposed in a housing of the device, each of the at least three sources including a diode and a lens positioned with respect to the diode to produce interrogating radiation, each of the at least three sources for simultaneously interrogating corresponding at least three unique retinal locations of the eye. The computer executable code may also obtain at least one candidate image of the total autofluorescence response of the lens of the eye as viewable through a pupil of the eye at a detector, the detector comprising an image sensor, and analyze the at least one candidate image of the total autofluorescence response of the lens of the eye as viewable through a pupil of the eye to determine a total lens autofluorescence index. Analyzing the at least one candidate image may include analyzing the at least one candidate image to determine a symmetry value and a definition value of a pupil spot of a pupil, analyzing the symmetry value and the definition value of the pupil to determine at least one confirmed image, discerning a median location of a peak of the at least one confirmed image, performing an average of an area of the median location of the peak of the at least one confirmed image, and determining the total lens autofluorescence index based on the average of the area of the median location of the peak of the at least one confirmed image.

DETAILED DESCRIPTION

Figure 1:
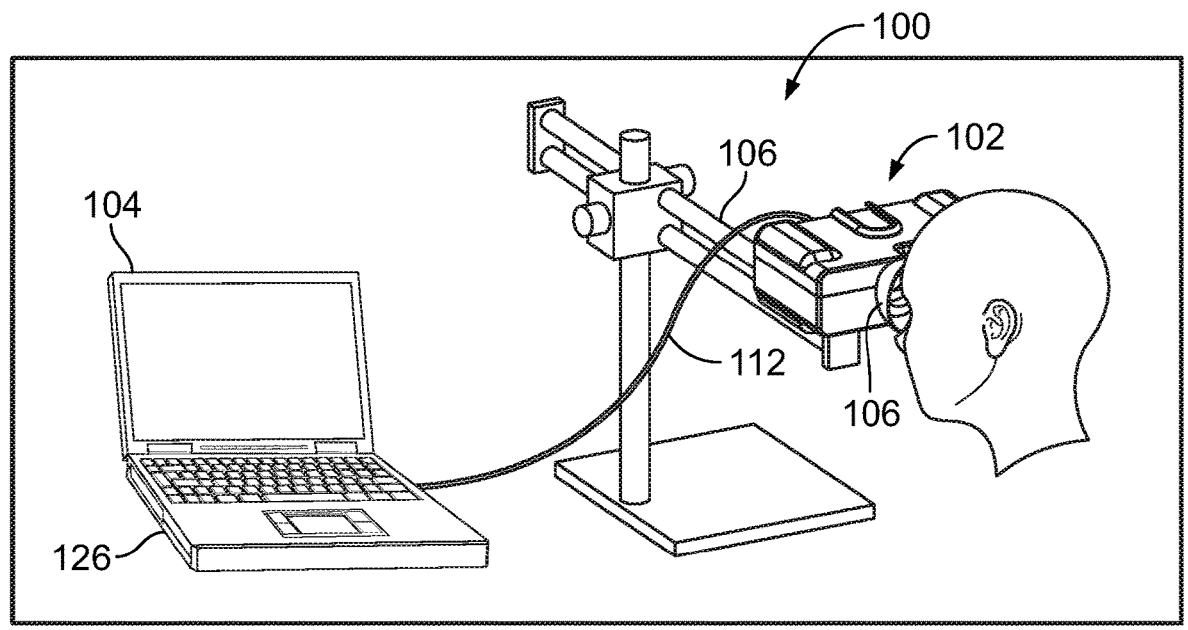
FIG. 1 illustrates an example system for determining a disease state based on total lens fluorescence in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

U.S. Pat. No. 5,203,328 to Samuels et al. entitled, "Apparatus and Methods for Quantitatively Measuring Molecular Changes in the Ocular Lens" is hereby incorporated by reference in its entirety. "Development of a noninvasive diabetes screening device using the ratio of fluorescence to Rayleigh scattered light" by Yu et al. (Journal of Biomedical Optics 1(3), 280-288 (July 1996)) is also hereby incorporated by reference in its entirety.

As used herein, "determining a disease state" shall mean determining the presence or likelihood of diabetes mellitus and/or dementia (e.g., Alzheimer's disease); the degree of progression of diabetes mellitus and/or dementia (e.g., Alzheimer's disease); a change in the presence, likelihood, or progression of diabetes mellitus and/or dementia (e.g., Alzheimer's disease); a probability of having, not having, developing, or not developing diabetes mellitus and/or dementia (e.g., Alzheimer's disease); the presence, absence, progression, or likelihood of complications from diabetes mellitus and/or dementia (e.g., Alzheimer's disease).

The terms "diabetes" and "diabetes mellitus" shall refer to a number of blood glucose regulation conditions, including Type I, Type II, and gestational diabetes, other types of diabetes as recognized by the American Diabetes Association including impaired fasting glucose (IFT), impaired glucose tolerance (IGT), and pre-diabetes.

The term "Alzheimer's disease" shall refer to a progressive degenerative disease of the brain that leads to dementia. Sometimes, It is considered as type-3 diabetes because it has molecular and biochemical features that overlap with both type-1 and type-2 diabetes mellitus. On a cellular level, Alzheimer's disease may be characterized by an extent of presence of neurofibrillary tangles in nerve cells of the brain. In the brain, Alzheimer's disease involves degeneration of the cortical regions, especially the frontal and temporal lobes.

The term "spectral response" shall refer to any ocular tissue reflectance characteristic indicative of one or more of a total autofluorescence response of a target tissue, a level of fluorescence intensity or a ratio of a level of fluorescence intensity to a level of scattered light, or any reflectance property of tissue that is useful for estimating the intrinsic fluorescence and Rayleigh scattering spectrum for a target tissue. In one non-limiting example, the spectral response can include one or more of the presence, intensity, change in intensity, or rate of change in intensity of autofluorescence of a target tissue at a select time and/or over a select period of time.

The term "level of FFI" means any measure of the presence, time, extent, state, or rate of accumulation of FFI in a target tissue associated with a disease state, including, as examples, measurements of the presence, concentration, or change in concentration of FFI in tissue; measurements of the rate or change in the rate of the accumulation of FFI; measurements of the presence, intensity, or change in intensity of fluorescence and the Rayleigh back scatter alone or, in combination, known to be associated with FFI; and measurements of the rate or change in the rate of the accumulation of FFI.

The term "obtain" or "obtaining", as used in connection with data, signals, measurements, information and the like, includes at least one of i) accessing memory of a local external device or resource manager where the data, signals, information, etc. are stored, ii) receiving the data, signals, information, etc. over a wireless communications link between the client device and a local external device, and/or iii) receiving the data, signals, information, etc. at a resource manager over a network connection. The obtaining operation, when from the perspective of a client device, may include sensing new signals in real time, and/or accessing memory to read stored data, signals, information, etc. from memory within the client device. The obtaining operation, when from the perspective of a local external device, includes receiving the data, signals, information, etc. at a transceiver of the local external device where the data, signals, information, etc. are transmitted from a client device and/or a resource manager. The obtaining operation may be from the perspective of a resource manager, such as when receiving the data, signals, information, etc. at a network interface from a local external device and/or directly from a client device. The resource manager may also obtain the data, signals, information, etc. from local memory and/or from other memory, such as within a cloud storage environment and/or from the memory of a workstation.

When light is described as having a "single wavelength" or a "peak wavelength", it is understood that the light can actually comprise light at a plurality of wavelengths, but that a significant portion of the energy in the light is transmitted at a single wavelength or at a range of wavelengths near a single wavelength (e.g., 430 nm with a tolerance of 10 nm, 495 nm with a tolerance of 20 nm, and the like).

FIG. 1 illustrates an example system for determining a disease state based on total lens fluorescence in accordance with embodiments herein. The system 100 includes a controller 102 that in one example is a total lens fluorescence (TLF) unit (e.g., a client device) for interrogating at least the lens of an eye by activating an illuminator for a select time and obtaining at least one measurement of the total autofluorescence response of the lens at a detector during or immediately following the select time in accordance with embodiments herein. The system 100 includes an remote device 104 that in one example is an electronic device (e.g., an external electronic device and/or a resource manager) operably coupled to the controller 102 for sending instructions to the controller 102, obtaining measurements of total lens fluorescence from the controller 102, and determining one or more disease states based on measurements of total lens fluorescence in accordance with embodiments herein. In one example, the controller 102 may be mounted on a stand 106 for stabilizing the controller 102.

Figure 2A:
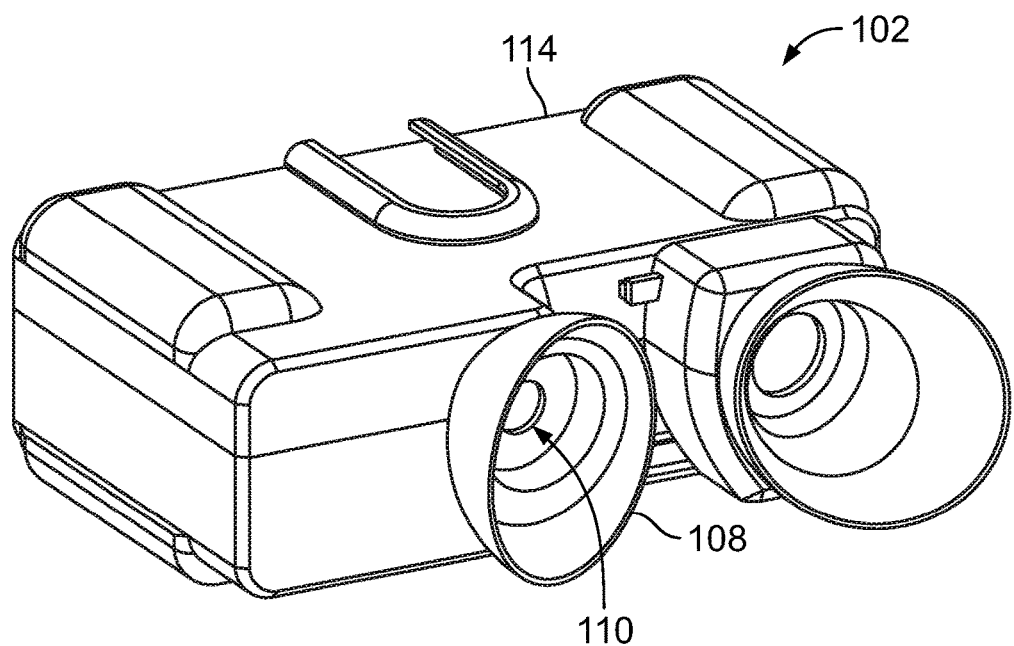
FIGS. 2A and 2B illustrate, respectively, a front perspective view and a rear perspective view of a device for determining a disease state based on total lens fluorescence in accordance with embodiments herein.
Figure 2B:
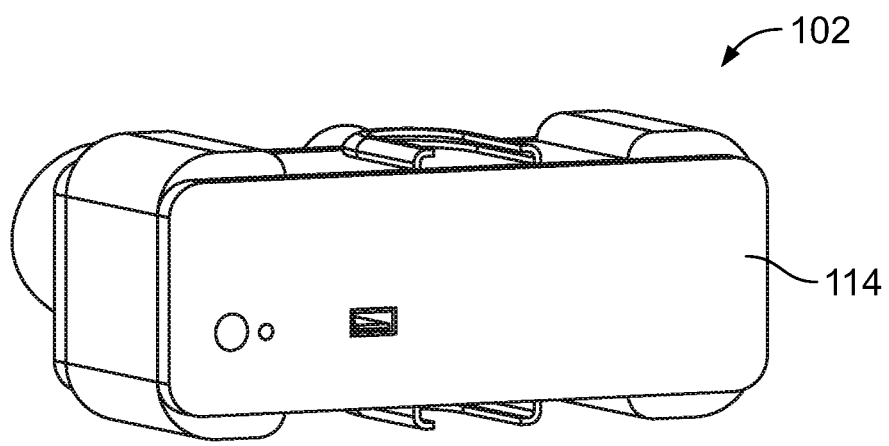

FIGS. 2A and 2B illustrate, respectively, a front perspective view and a rear perspective view of an example of a controller 102 for determining a disease state based on total lens fluorescence in accordance with embodiments herein. The controller 102 includes a housing 114 having an eye aperture 110 disposed therein through which measurements are obtained. In one example, the controller 102 may include at least one eyecup 108 disposed on an exterior of the housing 114 of the controller 102 about the eye aperture 110. The eye cup 108 receives the eye of the patient, positions the eye of the patient with respect to the aperture 110, and stabilizes the eye with respect to the illuminator and detector contained within the housing of the controller 102. In an example, the remote device 104 transmits instructions to and obtains data from the controller 102 over a wired connection 112 (e.g., a USB cable, or the like). In an additional or alternative example, the remote device 104 transmits instructions to and obtains data from the controller 102 over a wireless connection (e.g., a network connection, Bluetooth connection, or the like).

Figure 3:
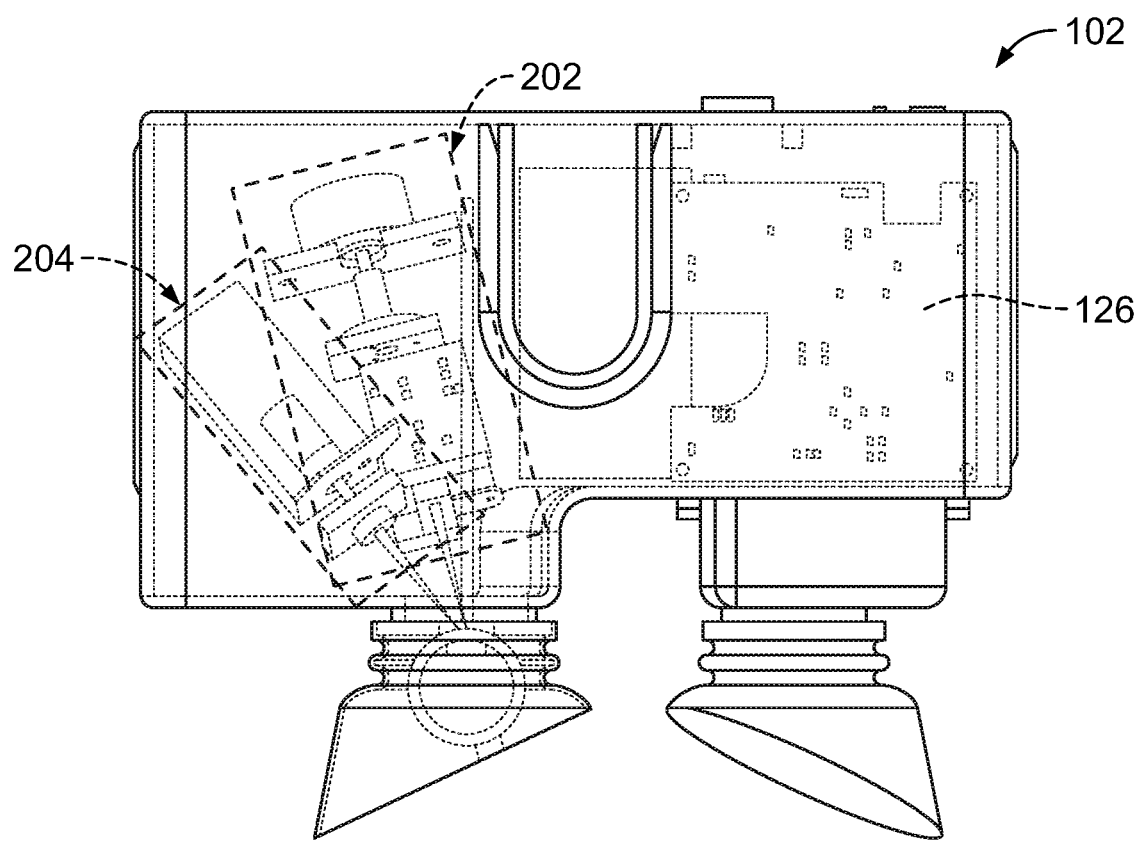
FIG. 3 illustrates example aspects of the device of FIGS. 2A and 2B in accordance with embodiments herein.
Figure 4:
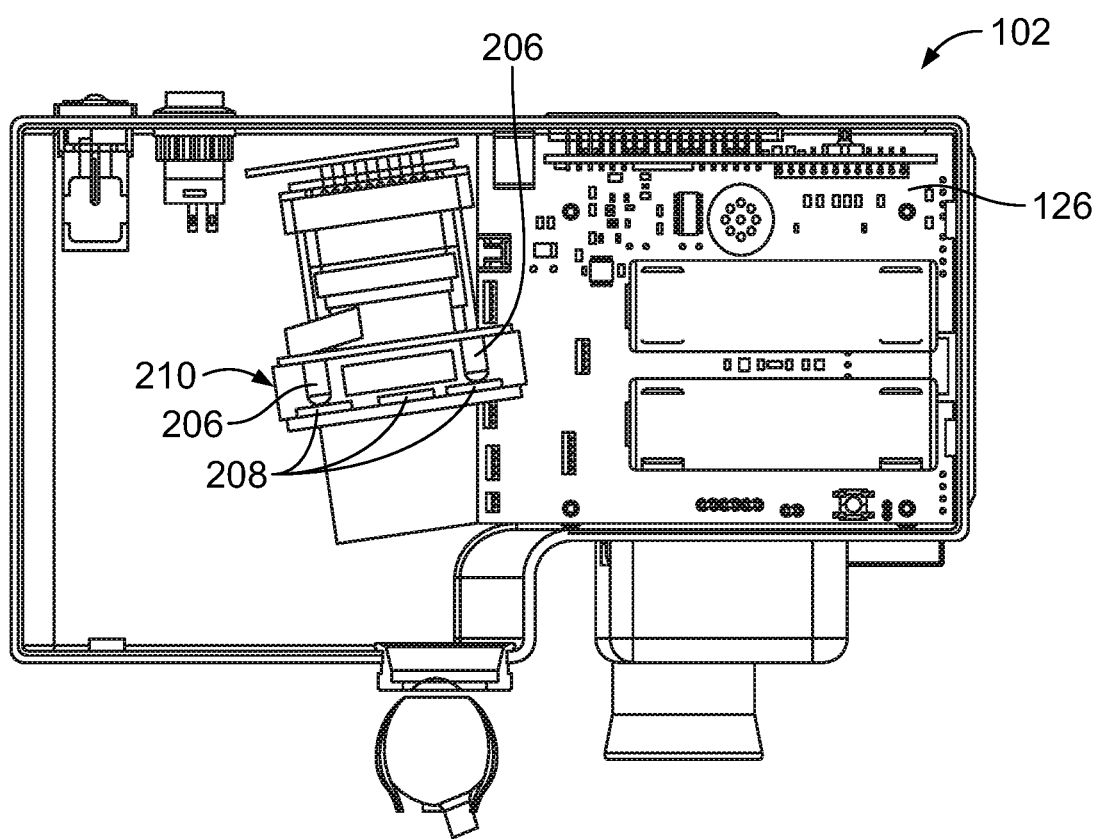
FIG. 4 illustrates example aspects of the device of FIGS. 2A and 2B in accordance with embodiments herein.

FIGS. 3 and 4 illustrate example aspects of the controller 102 of FIGS. 2A and 2B. The controller 102 interrogates at least the lens of an eye by activating an illuminator 202 for a select time and obtaining at least one measurement of the total autofluorescence response of the lens at a detector 204 during or immediately following the select time in accordance with embodiments herein. The illuminator 202 includes at least one light source 206 (e.g., a light-emitting diode (LED), a laser, and the like) for generating excitation radiation for illuminating a target tissue L of an eye of a patient, at least one lens 208 positioned with respect to the at least one light source 206 to produce interrogating radiation. The at least one light source 206 may be fixed with respect to the eye aperture 110 disposed in the housing 114. The at least one light source 206 may have a peak wavelength of 430 nm. The at least one light source 206 may produce blue and/or violet light. The at least one light source 206 may include a laser diode or a light-emitting diode (LED). In one example, the light source 206 includes a Thorlabs 430 L LED. In the example, the light source 206 may emit 8 mw of light from an approximately 100 micron diameter LED that may be at least partially collimated by a 3 mm ball lens into a 22 degree cone. The illuminator 202 may also include a narrow bandpass filter positioned between the at least one light source and the eye aperture 110. In one example, the light from the light source 206 is filtered by a filter 212. The filter 212 may be a high efficiency narrowband filter with a bandpass of 17-20 nm centered on 435 nm. The filter 212 may reduce the total output power of the light source 206 (e.g., from 8 mw to 4 mw). A surface of the filter 212 may be positioned 6 cm from a nominal eye position as measured from the cornea of the eye of a patient. The detector 204 includes an image sensor 214. The image sensor 214 may include a digital camera unit to image the total fluorescence response of the eye during or immediately after exposure to interrogating radiation from the light source 206. In one example, the image sensor is has a linear response to light intensity. The image sensor 214 may be a digital camera unit that may be a 5 MP camera. The detector 204 may also include a detector filter 216 positioned between the image sensor 214 and the eye aperture 110. In one example, the filter 216 may be centered on 495 nm with a bandpass of 17-20 nm.

Figure 5:
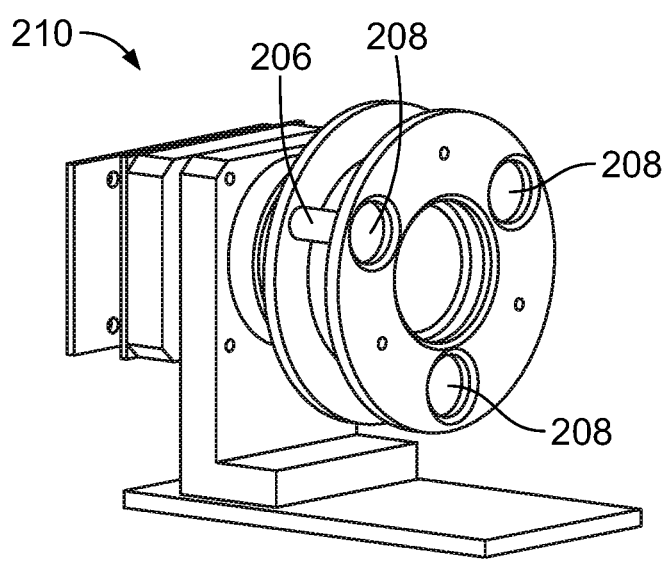
FIG. 5 illustrates an example of an illumination wheel in accordance with embodiments herein.
Figure 6:
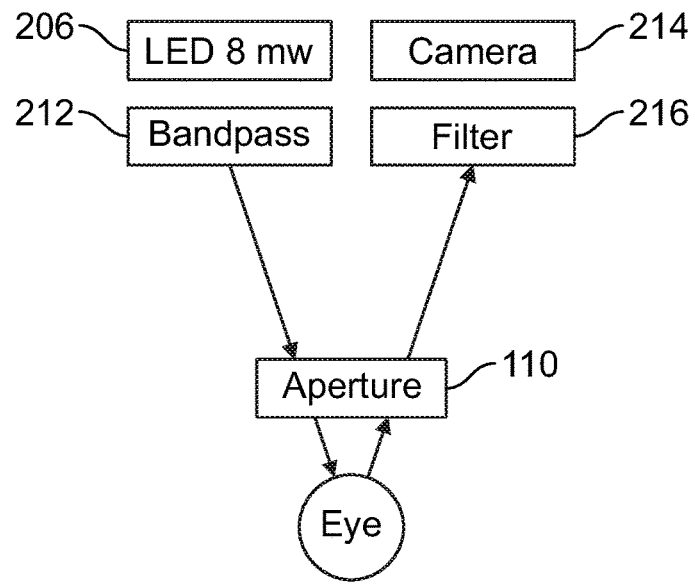
FIG. 6 illustrates one example of an optical arrangement in accordance with embodiments herein.

Optionally, the light source 206 may include an illumination wheel 210 (shown in at least FIGS. 4 and 5) and the at least one light source 206 may include an array of light sources 206 (e.g., 3) that are spaced about a central point of an illumination wheel 210. The array of light sources 206 may be radially equally spaced about the central point. Each of the at least three light sources 206 may be configured to interrogate corresponding at least three unique retinal locations. Each of the at least three light sources 206 may be pulsed on and off at unique intervals with respect to the remaining ones of the at least three light sources 206.

Division and processing of responding radiation received by the detector 204 may occur in the detection and processing assembly (DPA) 126. The DPA 126 may be implemented on, or partially on, one or both of the controller 102 and the external remote device 104.

The DPA 126 may include components such as one or more processors 152 (e.g., a microprocessor, microcomputer, application-specific integrated circuit, etc.), one or more local storage medium (also referred to as a memory) 154, a user interface 144 which includes one or more input circuits 145 and one or more output circuits 148, a power module 156, a component interface 158, and one or more wireless transceivers 162. All of these components can be operatively coupled to one another, and can be in communication with one another, by way of one or more internal communication links, such as an internal bus.

The input circuit 145 receives user instructions in various manners at the user interface 144. The processors 152 execute instructions stored in the memory 154 to interpret and perform actions based on user instructions that are received through the input circuit 145. The user instruction may be an instruction to perform one or more measurements of the target tissue or an instruction to perform various types of actions and/or execute various types of commands, as described herein.

Figure 7:
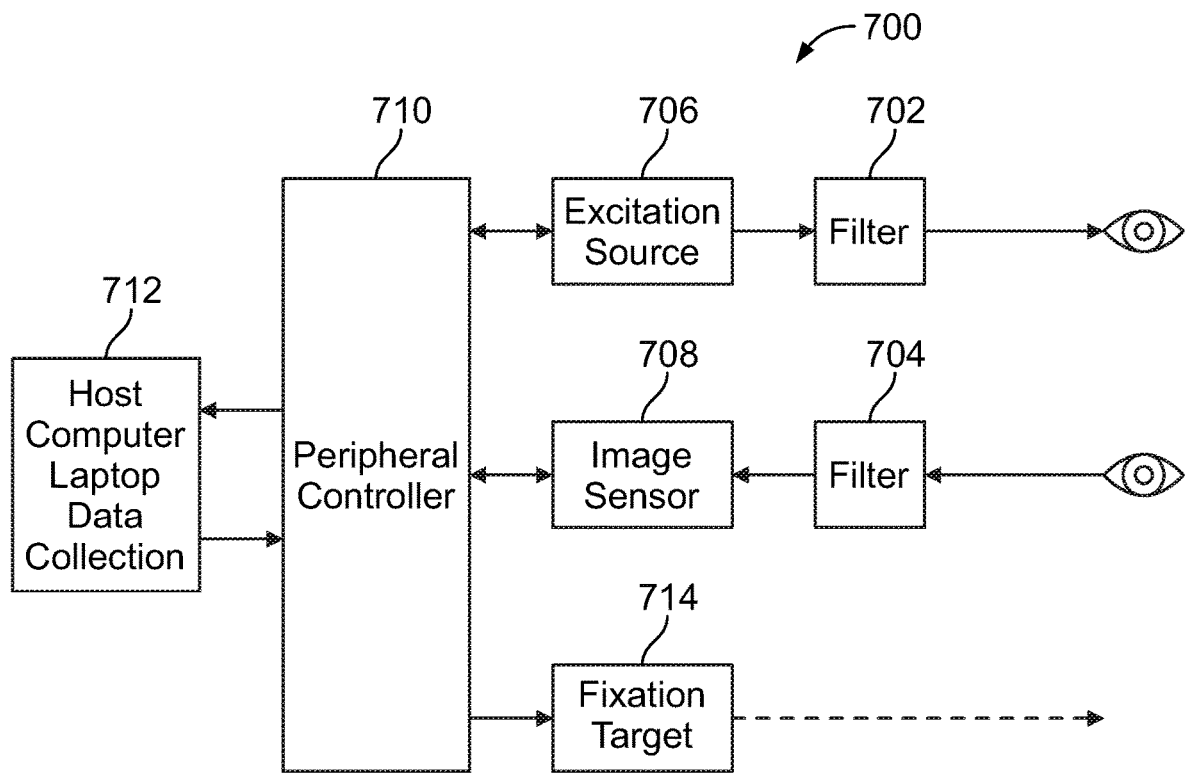
FIG. 7 illustrates aspects of operation of the system of FIG. 1 and a process for obtaining measurements of total lens fluorescence in accordance with embodiments herein.

An emitted radiation analysis (ERA) application 160, operating in accordance with reference to FIG. 7, among other things, receives user-generated instructions to perform one or more measurements on a target tissue and, based thereon, discriminates an autofluorescence response of a target tissue of an eye due to a current level of FFI in the target tissue. FFI is 2-(2-FUROYL)-4(5)-2(FURANYL)-1H IMIDAZOLE. Specifically, FFI is one of the 36 known advanced glycation end-products (AGEs) having a chemical structure with extensive π-conjugation. It is cross-linked with protein two lysine residues. This AGE, because of its extensive π-conjugation, is the only one among the 36, having the longest wavelength (maximum at 375 nm) of absorbance extending to visible region (400-460 nm). Despite all the in vitro chemical evidence (1-3) questioning its existence in vivo, the spectroscopic data do show formation of "FFI-like" AGE in the eye lens protein, as well as, in the intact lenses upon non-enzymatic glycation of bovine lens a-crystallin and human lenses (4).

The ERA application 160 interrogates at least a lens of an eye by activating the illuminator for a select time. The illuminator includes at least one light source and a lens positioned with respect to the light source to produce interrogating radiation. The at least one light source may be fixed relative to an eye aperture disposed in a housing of the device. The ERA application 160 obtains at least one image of the total autofluorescence response of the lens of the eye as viewable through a pupil of the eye from the detector. The detector is operable to image the total autofluorescence response of the lens. The detector includes, as a sensor, a digital camera unit. The ERA application 160 may activate the illuminator for a select time (e.g., 2 s) per measurement and, during or immediately subsequent to the select time, activate the detector to obtain at least one image corresponding to the measurement. The ERA application 160 may sequentially perform 2 to 30 measurements. The ERA application 160 transmits the at least one image to a remote electronic device via one or more of a wired or a wireless connection. In one example, the ERA application 160 illuminates the target tissue L of the eye with excitation radiation having a peak wavelength of 430 nm and measures the autofluorescence response of the target tissue due to the current level of FFI. In an example, the at least one light may include an array of at least three light sources and the ERA application 160 may interrogate the lens of the eye by pulsing each of the at least three light sources on and off at unique intervals with respect to the remaining ones of the at least three sources. The ERA application 160 may transmit the at least one image to a remote electronic device via one or more of a wired or a wireless connection.

The DPA 126 includes an output circuit 148 and one or more wireless transceivers 162, one or both of which may output measurements of the target tissue and related data, and associated requests, to one or more remote electronic devices over a network 111. The DPA 126 may be configured to access the network 111 over a wired or wireless connection. As non-limiting examples, the DPA 126 may access the network 111 through a wireless communications channel and/or through a network connection (e.g., the Internet). Additionally or alternatively, the DPA 126 may include a wired or wireless communication terminal, such as a desktop computer, laptop computer, and the like.

The DPA 126 may be configured to access the network resources 118, including web-based or network-based data, applications, and services, via the network 111. The network 111 may represent one or more of a local area network (LAN), a wide area network (WAN), an Intranet or other private network that may not be accessible by the general public, or a global network, such as the Internet or other publicly accessible network. The network 111 provides communication between the DPA 126, one or more remote electronic device, and one or more network resources 118. It will be understood that, in some embodiments, the network resources 118 may represent a single entity or one or more physical or virtual servers that are configured to deliver online resources to the DPA 126. Examples of the network resources 118 include, but are not limited to, web-based or network-based data storage services, web-based or network-based patient management services, and the like.

The user interface 144 permits the user to operate the DPA 126 for any of its intended purposes, such as administering the ERA application 160, operating software applications, electronic communication, and the like. The input circuit 145 can include one or more of a visual input device, such as an optical sensor or camera, and/or a mechanical input circuit such as a keyboard, keypad, selection hard and/or soft buttons, switch, touchpad, touch screen, icons on a touch screen, a touch sensitive areas on a touch sensitive screen and/or any combination thereof that are configured to receive input (e.g., instructions, requests) from the user. The output 148 can include one or more electronic devices, such as a display 166, that are configured to communicate output measurements of the target tissue and related data and/or content to the user. For example, the output circuit 148 can include a visual output circuit such as a liquid crystal display screen, touch sensitive screen, a non-touch sensitive screen, a text-only display, a smart phone display, an audio output (e.g., a speaker or headphone jack), and/or any combination thereof and/or one or more light emitting diode indicators. The output circuit 148 is integral to (e.g., within a common housing) at least the DPA 126.

The memory 154 may encompass one or more memory devices of a variety of forms (e.g., read only memory, random access memory, static random-access memory, dynamic random-access memory, etc.) and can be used by the processor 152 to store and retrieve data. The data that is stored by the memory 154 can include, but need not be limited to, operating systems, applications, user collected content, and informational data. Each operating system includes executable code that controls basic functions of the device, such as interaction among the various components, communication with external devices via the wireless transceivers 162, the component interface 158, and storage and retrieval of applications and data to and from the memory 154. Each application includes executable code that utilizes an operating system to provide more specific functionality for the communication devices, such as file system service and handling of protected and unprotected data stored in the memory 154.

The memory 154 stores various content including, but not limited to, the ERA application 160. The ERA application 160 includes instructions accessible by the one or more processors 152 to direct the processor 152 to implement the methods, processes and operations described herein including, but not limited to, the methods, processes and operations illustrated in the Figures and described in connection with the Figures. In an alternative embodiment, the ERA application 160 may operate from one or more storage medium (also referred to as cloud storage).

FIG. 7 illustrates a schematic block diagram of a system 700 for determining a disease state based on total lens fluorescence. The system 700 includes a first filter 702 and a second filter 704. Each filter may be a high efficiency narrowband filter with a bandpass of 17-20 nm centered on 435 nm. The first filter 702 may reduce the total output power of an excitation source 706 that in one example is a light source (e.g., from 8 mw to 4 mw). Meanwhile, the second filter 704 filters an image before the image is received by an image sensor 708. A controller 710 is operably coupled to the excitation source 706 and image sensor 708 such as a detector to control the output of the excitation source 706, and receive image data from the image sensor that may be utilized as feedback. The controller 710 may also be coupled to a remote computing device 712 for storing data, images, etc. Based on the filtering, the controller 710 determines a fixation target 714.

Figure 8:
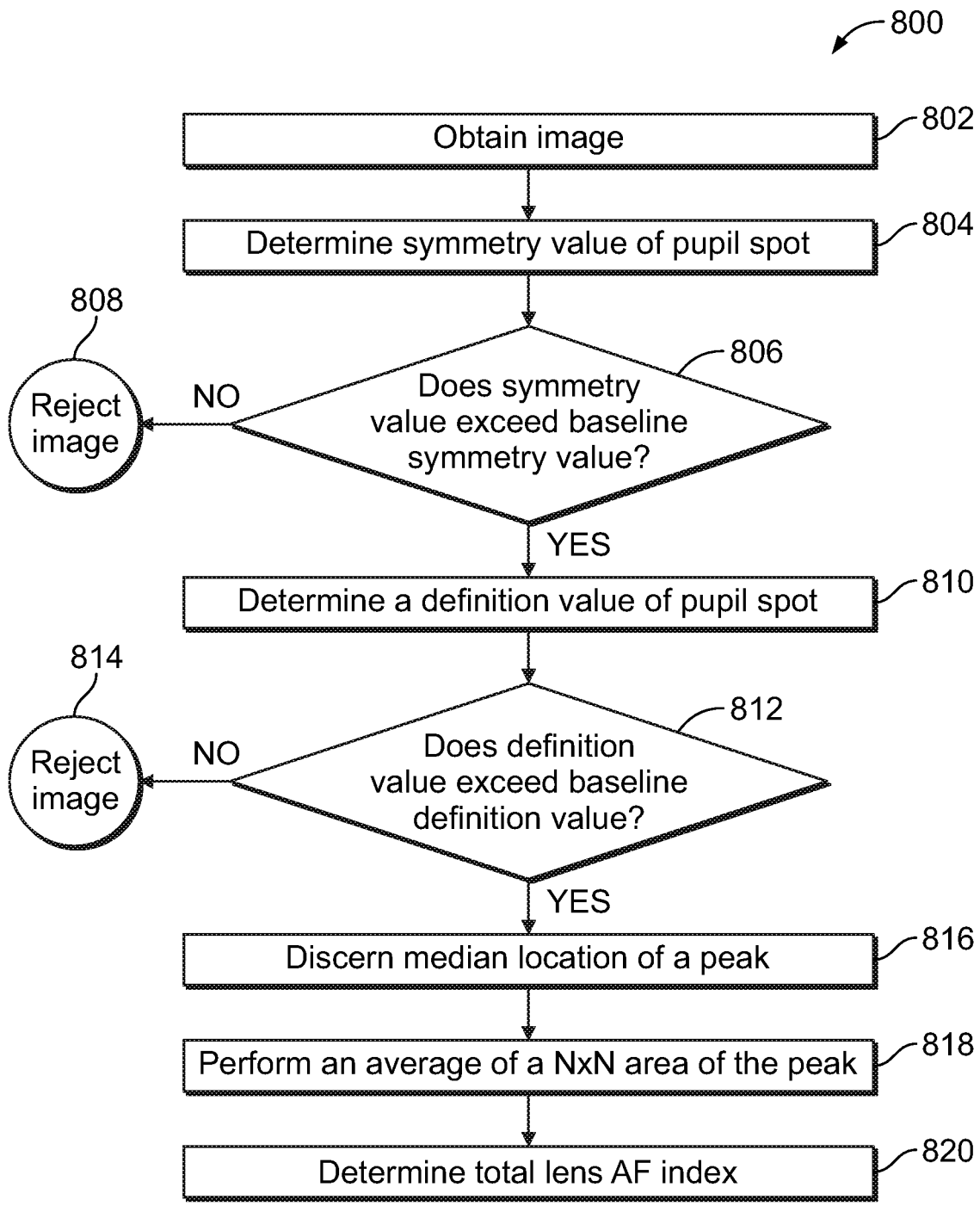
FIG. 8 illustrates a block flow diagram of a process for determining a disease state in accordance with embodiments herein.

FIG. 8 illustrates a method 800 for determining a disease state based on autofluorescence of a tissue. Determining a disease state includes determining a disease state based on autofluorescence due to the accumulation of FFI in a target tissue. In one example, the method 800 is performed utilizing the systems and methods described in detail in relation to FIGS. 1-7. A portion of the operations of FIG. 8 may be implemented by one or more processors of the optical system 100 configured with executable instructions. It should be recognized that while the operations of method 800 are described in a somewhat serial manner, one or more of the operations of method 800 may be continuous and/or performed in parallel with one another. For example, the various operations of the optical system 100 may be continuous and/or performed in parallel with one another and/or other functions of the optical system.

At 802, one or more processors obtain an image. In one example, the image is obtained from an image sensor that may include a digital camera. In another example, a scanning system is utilized that scans through the lens of the eye using an off visual axis focused LED beam at 430 nm and 472 nm that measures fluorescence and scattering. Alternatively, the starting system floods the eye with light from a 430 nm blue LED and utilizes a digital camera to take a picture of the fluorescence from the lens of the eye as viewed through the pupil.

At 804, the one or more processors determine the symmetry value of a pupil spot. In one example, the one or more processors interrogate the pupil based on image data obtained from the digital camera. In order to make the determination, the one or more processors may utilize an algorithm, mathematical equation, mathematical function, mathematical model, lookup table, decision tree, etc.

At 806, the one or more processors determine whether the symmetry value of the pupil spot exceeds a baseline symmetry value. The baseline symmetry value may be obtained from a storage device or memory of a controller, a remote device, or the like. The determination may be made utilizing an algorithm, mathematical equation, mathematical function, mathematical model, lookup table, decision tree, etc. If at 806 the symmetry value does not exceed the baseline symmetry value, at 808, the one or more processors reject the image. If at 806, the one or more processors determine that the symmetry value does exceed the baseline symmetry value, then at 810, the one or more processors determine a definition value of the pupil spot. The definition value may be determined utilizing an algorithm, mathematical equation, mathematical function, mathematical model, lookup table, decision tree, etc.

At 812, the one or more processors determine if the definition value exceeds a baseline definition value. If not, at 814 the image is rejected. If the definition value exceeds the baseline definition value, at 816 one or more processors discern a median location of a peak is determined. In one example, the discernment is made using methodologies as described in relation to FIG. 9.

At 818, the one or more processors perform an average of an N by N area of the peak. Specifically, the median location of the peak may comprise at least an N by N area of pixels of the image. In one example, the N by N area comprises at least a 5 pixel by 5 pixel area. In another example the N by N area is in a range from a 5 pixel by 5 pixel area to a 25 pixel by 25 pixel area.

At 820, the one or more processors determine a total lens autofluorescence (AF) index. In particular, the one or more processors determine the total lens AF range for the patient in order to make diagnosis accordingly.

Figure 9:
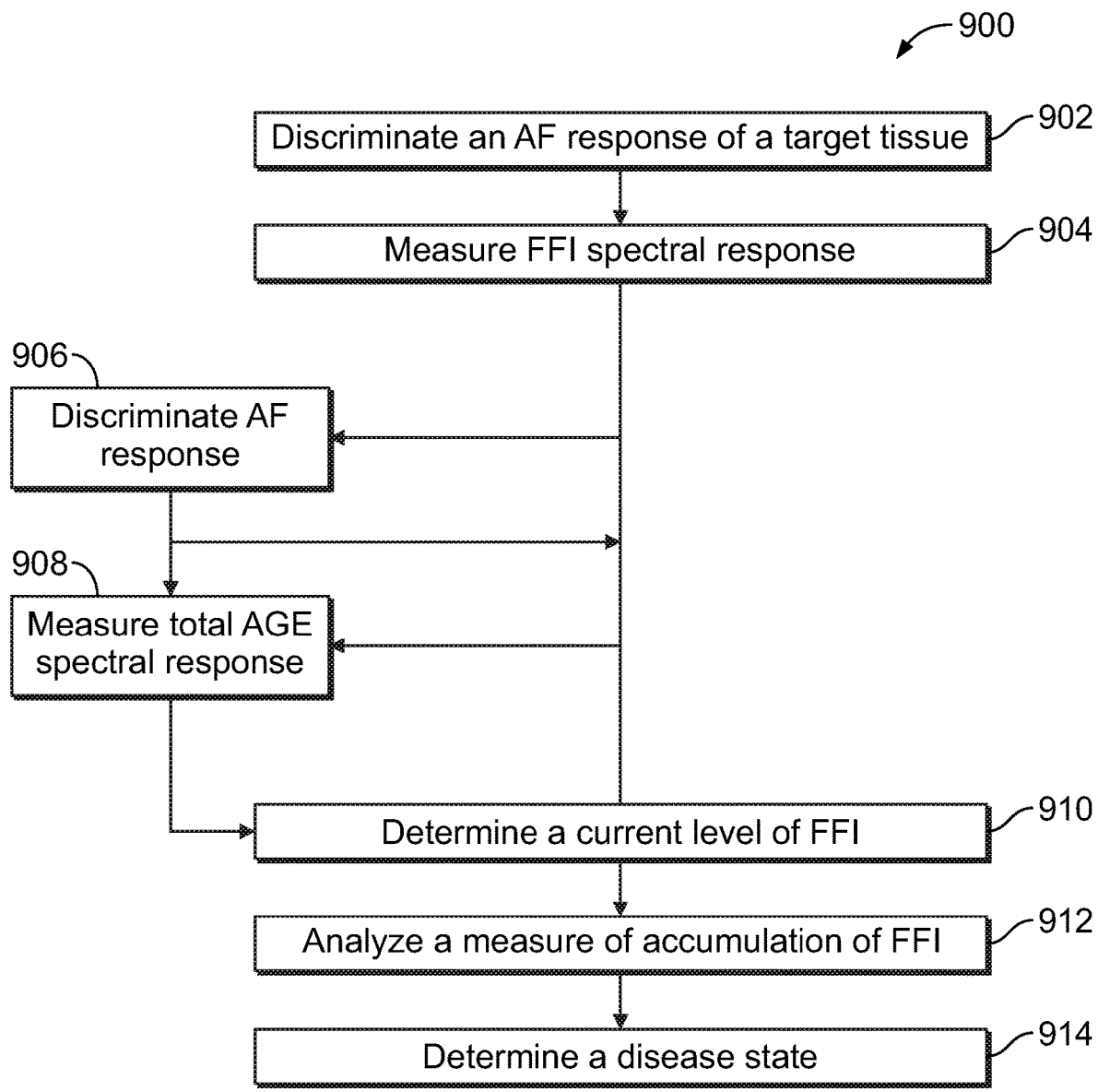
FIG. 9 illustrates a block flow diagram of a process for determining a disease state in accordance with embodiments herein.

FIG. 9 illustrates an example process for determining a disease state based on discriminating an autofluorescence response of a target tissue due to FFI in accordance with embodiments herein. In one example, the method 900 is performed utilizing the systems and methods described in detail in relation to FIG. 1. A portion of the operations of FIG. 9 may be implemented by one or more processors of the optical system 100 configured with executable instructions. It should be recognized that while the operations of method 900 are described in a somewhat serial manner, one or more of the operations of method 900 may be continuous and/or performed in parallel with one another. For example, the various operations of the optical system 100 may be continuous and/or performed in parallel with one another and/or other functions of the optical system.

Beginning at 902, one or more processors of the DPA 126 discriminate an autofluorescence (AF) response of a target tissue of an eye due a current level of FFI in the target tissue. Discriminating the autofluorescence response due to the current level of FFI includes minimizing or eliminating any autofluorescence response due to the presence of any other AGE. The discriminating operation includes illuminating the target tissue L with excitation radiation having a peak wavelength of 430 nm. For example, the one or more processors of the DPA direct the at least one light source 206 to illuminate a target tissue L of an eye with the excitation radiation having a peak wavelength of 430 nm and a tolerance of 10 nm. The target tissue L includes a crystalline lens.

At 904, one or more processors of the DPA 126 measure, as the autofluorescence response of the target tissue due to the current level of FFI, an FFI spectral response of the target tissue. For example, the one or more processors direct the detector 204 to measure the FFI spectral response of the target tissue L. The FFI spectral response of the target tissue may include a total autofluorescence. The process may measure, as the FFI spectral response, one or more of the presence, intensity, change in intensity, or rate of change in intensity of autofluorescence over a select time. Optionally, the process may measure an ensemble of FFI spectral responses and utilize a mathematical operation (e.g., averaging, mean, median, and the like) to combine the spectral responses to form resultant spectral response.

Optionally, at 906, one or more processors of the DPA 126 discriminating an autofluorescence response of the target tissue due to a current level of all advanced glycation end products (AGEs) in the target tissue. The discriminating operation includes illuminating the target tissue L with excitation radiation having a peak wavelength of 375 nm. For example, the one or more processors of the DPA direct the at least one light source 206 to illuminate a target tissue L of an eye with the excitation radiation having a peak wavelength of 375 nm and a tolerance of 10 nm.

Optionally, at 908, the one or more processors of the DPA 126 measure, as the autofluorescence response of the target tissue due to the current level of all AGEs in the target tissue, a total AGE spectral response of the target tissue. For example, the one or more processors direct the detector 204 to measure the total AGE spectral response of the target tissue L. The total AGE spectral response of the target tissue may include one or more of a total autofluorescence, a level of fluorescence intensity or a ratio of a level of fluorescence intensity to a level of scattered light. The process may measure, as the total AGE spectral response, one or more of the presence, intensity, change in intensity, or rate of change in intensity of autofluorescence over a select time. Optionally, the process may measure an ensemble of total AGE spectral responses and utilize a mathematical operation (e.g., averaging, mean, median, and the like) to combine the spectral responses to form resultant spectral response.

At 910, one or more processors of the DPA 126 determine a current level of FFI in the target tissue L based on at least the spectral response of the target tissue L. The process may determine the presence, concentration, change in concentration, or rate of change in concentration of FFI over a select time. Optionally, at 906, one or more processors of the DPA 126 determine, as the current level of FFI, the ratio of the FFI spectral response to the total AGE spectral response of the target tissue. Optionally, the process may, based on measuring an ensemble of FFI and/or total AGE spectral responses and utilizing a mathematical operation (e.g., averaging, mean, median, and the like) to combine the FFI and/or total AGE spectral responses to form resultant spectral response, analyze the resultant spectral response to determine the current level of FFI in the target tissue L.

At 912, one or more processors of the DPA 126 analyze a measure of accumulation of FFI. The analyzing includes analyzing the current level of FFI in the target tissue and one or more previous levels of FFI in the target tissue. The process may, as part of analyzing, determine changes in one or more of the level of fluorescence or the scattering spectra associated with one or more of the current level of FFI or changes in the level of FFI over a select time. Additionally or alternatively, the process may, as part of analyzing, compare the current level of FFI to a baseline level of FFI obtained from the patient in a disease-free condition. Additionally or alternatively, the process may, as part of analyzing, compare the current level of FFI to one or more baseline level of FFI obtained from one or more of an age-normed, a gender-normed, or an ethnicity-normed control value. Optionally, the process may analyze an ensemble of a measure of accumulation of FFI and utilize a mathematical operation (e.g., averaging, mean, median, and the like) to combine the ensemble of the measure of accumulation of FFI to form a resultant measure of accumulation of FFI.

At 914, one or more processors of the DPA 126 determine a disease state of a patient. The disease state may include one or more of a diabetic disease state or an Alzheimer's disease state. The process determines a disease state of the patient based on one or more measure of accumulation of FFI falls within or outside of one or more threshold value (e.g., above or below one or more threshold value). For example, a threshold may be established based on analyzing values for a normed population of individuals (e.g., age-normed, gender-normed, ethnicity-normed, and the like) based on known disease states for each of the individuals.

A list of numbered examples of the present subject matter include:

Example 1 is a device, comprising: an illuminator operable to interrogate at least a lens of an eye, the illuminator comprising at least one light source and a lens positioned with respect to the light source to produce interrogating radiation, wherein the at least one light source is fixed relative to an eye aperture disposed in a housing of the device; a detector operable to image the total autofluorescence response of the lens of the eye as viewable through a pupil of the eye, the detector comprising an image sensor; a controller operable to control operation of the illuminator and the detector, wherein the controller includes, an input to receive an instruction to perform an action, one or more processors, and a memory storing program instructions accessible by the one or more processors, wherein, responsive to execution of the program instructions, the one or more processors perform the following: interrogate at least the lens of the eye by activating the illuminator for a select time; obtain at least one image of the total autofluorescence response of the lens at the detector during or immediately subsequent to the select time; and transmit the at least one image to a remote electronic device.

In Example 2, the subject matter of Example 1 includes, wherein the at least one light source has a peak wavelength of 430 nm.

In Example 3, the subject matter of Examples 1-2 includes, wherein the at least one light source comprises an array of at least three sources that are spaced about to a central point.

In Example 4, the subject matter of Example 3 includes, wherein the at least three light sources are equally radially spaced about the central point.

In Example 5, the subject matter of Examples 3-4 includes, wherein each of the at least three light sources are configured to interrogate corresponding at least three unique retinal locations In Example 6, the subject matter of Examples 3-5 includes, wherein each of the at least three light sources are pulsed on and off at unique intervals with respect to the remaining ones of the at least three light sources.

In Example 7, the subject matter of Examples 1-6 includes, wherein the light source includes a laser diode or a light-emitting diode (LED).

In Example 8, the subject matter of Examples 1-7 includes, wherein the illuminator further comprises a narrow bandpass filter positioned between the at least one light source and the eye aperture.

In Example 9, the subject matter of Examples 1-8 includes, a visible target to facilitate alignment of the eye with the detector.

In Example 10, the subject matter of Examples 1-9 includes, an eyecup disposed on an exterior of the housing about the eye aperture for receiving and stabilizing the eye with respect to the illuminator and the detector.

In Example 11, the subject matter of Examples 1-10 includes, wherein the detector further comprises a detector filter disposed between a sensor of the detector and the eye aperture.

Example 12 is a method, comprising: under control of one or more processors configured with executable instructions: interrogating at least a lens of an eye by activating an illuminator for a select time, the illuminator comprising at least one light source and a lens positioned with respect to the light source to produce interrogating radiation, wherein the at least one light source is fixed relative to an eye aperture disposed in a housing of the device; obtaining at least one image of the total autofluorescence response of the lens of the eye as viewable through a pupil of the eye from a detector, the detector operable to image the total autofluorescence response of the lens, the detector comprising an image sensor; and transmitting the at least one image to a remote electronic device.

In Example 13, the subject matter of Example 12 includes, wherein the at least one light source includes a light-emitting diode (LED).

In Example 14, the subject matter of Examples 12-13 includes, as part of the interrogating, flooding the lens of the eye with interrogating radiation between 420 nm and 440 nm.

In Example 15, the subject matter of Examples 12-14 includes, wherein the one or more processors are further configured to activate the illuminator for a select time per measurement and, during or immediately subsequent to the select time, activate the detector to obtain at least one image corresponding to the measurement.

In Example 16, the subject matter of Example 15 includes, wherein the select time is from 2 seconds to 30 seconds.

In Example 17, the subject matter of Examples 15-16 includes, wherein the one or more processors are further configured to sequentially perform 2 to 30 measurements.

In Example 18, the subject matter of Examples 12-17 includes, wherein transmitting further comprises transmitting the at least one image to the remote electronic device via a wired connection.

In Example 19, the subject matter of Examples 12-18 includes, wherein transmitting further comprises transmitting the at least one image to the remote electronic device via a wireless connection over a network.

In Example 20, the subject matter of Examples 12-19 includes, wherein the at least one light source further comprises an array of at least three light sources and interrogating includes pulsing each of the at least three light sources on and off at unique intervals with respect to the remaining ones of the at least three sources.

Example 21 is a method, comprising: analyzing a plurality of candidate images of the total autofluorescence response of the lens of the eye as viewable through a pupil of the eye, wherein analyzing each image of the plurality of candidate images comprises: analyzing the image to determine a symmetry value and a definition value of a pupil spot of a pupil; analyzing the symmetry value and the definition value of the pupil to determine at least one confirmed image; discerning a median location of a peak of the at least one confirmed image; performing an average of an area of the median location of the peak of the at least one confirmed image; and determining a total lens autofluorescence index based on the average of the area of the median location of the peak of the at least one confirmed image.

In Example 22, the subject matter of Example 21 includes, wherein the median location of the peak comprises at least an N by N area of pixels of the image.

In Example 23, the subject matter of Examples 21-22 includes, wherein the at least and N by N area comprises at least a 5 pixel by 5 pixel area.

In Example 24, the subject matter of Examples 21-23 includes, wherein the at least an N by N area is from a 5 pixel by 5 pixel area to a 25 pixel by 25 pixel area.

In Example 25, the subject matter of Examples 21-24 includes, wherein determining the total lens autofluorescence index comprises determining a total lens autofluorescence value based on the plurality of images normalized by the area of the median location to determine a normalized total lens autofluorescence value.

In Example 26, the subject matter of Example 25 includes, wherein determining the total lens autofluorescence index further comprises normalizing the normalized total lens autofluorescence value with a calibration value.

In Example 27, the subject matter of Example 26 includes, wherein the calibration value comprises a total lens calibration autofluorescence index.

In Example 28, the subject matter of Examples 25-27 includes, wherein determining the total lens calibration autofluorescence index comprises determining a total lens calibration autofluorescence value based on at least one calibration image normalized by the area of the calibration median location to determine the total lens calibration autofluorescence value.

In Example 29 the subject matter of Examples 21-28 includes, wherein the total lens calibration autofluorescence index is used to determine a disease state of the patient.

Example 30 is a computer program product comprising a non-signal computer readable storage medium comprising computer executable code to: interrogate at least a lens of an eye by activating an illuminator for a select time, the illuminator comprising an array of at least three sources that are spaced about to a central point, each of the at least three sources fixed relative to an eye aperture disposed in a housing of the device, each of the at least three sources including a diode and a lens positioned with respect to the diode to produce interrogating radiation, each of the at least three sources for simultaneously interrogating corresponding at least three unique retinal locations of the eye; obtain at least one candidate image of the total autofluorescence response of the lens of the eye as viewable through a pupil of the eye at a detector, the detector comprising an image sensor; analyze the at least one candidate image of the total autofluorescence response of the lens of the eye as viewable through a pupil of the eye to determine a total lens autofluorescence index, wherein analyzing the at least one candidate image comprises: analyze the at least one candidate image to determine a symmetry value and a definition value of a pupil spot of a pupil; analyze the symmetry value and the definition value of the pupil to determine at least one confirmed image; discern a median location of a peak of the at least one confirmed image; perform an average of an area of the median location of the peak of the at least one confirmed image; and determine the total lens autofluorescence index based on the average of the area of the median location of the peak of the at least one confirmed image.

In Example 31, the subject matter of Example 30 includes, wherein the median location of the peak comprises at least an N by N area of pixels of the image.

In Example 32, the subject matter of Examples 30-31 includes, wherein the at least and N by N area comprises at least a 5 pixel by 5 pixel area.

In Example 33, the subject matter of Examples 30-32 includes, wherein the at least an N by N area is from a 5 pixel by 5 pixel area to a 25 pixel by 25 pixel area.

In Example 34, the subject matter of Examples 30-33 includes, computer executable code to, as part of the determine the total lens autofluorescence index, determine a total lens autofluorescence value based on the plurality of images normalized by the area of the median location to determine a normalized total lens autofluorescence value.

In Example 35, the subject matter of Example 34 includes, computer executable code to, as part of the determine the total lens autofluorescence index, normalize the normalized total lens autofluorescence value with a calibration value.

In Example 36, the subject matter of Example 35 includes, wherein the calibration value comprises a total lens calibration autofluorescence index.

In Example 37, the subject matter of Example 36 includes, computer executable code to, as part of the determine the total lens autofluorescence index, determine a total lens calibration autofluorescence value based on at least one calibration image normalized by the area of the calibration median location to determine the total lens calibration autofluorescence value.

In Example 38, the subject matter of Examples 30-37 includes, wherein the diode comprises a light-emitting diode (LED).

In Example 39, the subject matter of Examples 29-37 includes, wherein, as part of the interrogating, flooding the lens of the eye with interrogating radiation between 420 nm and 440 nm.

In Example 40, the subject matter of Examples 30-39 includes, wherein the one or more processors are further configured to activate the illuminator for a select time per measurement and, during or immediately subsequent to the select time, activate the detector to obtain at least one image corresponding to the measurement.

In Example 41, the subject matter of Example 40 includes, wherein the one or more processors are further configured to sequentially perform 2 to 30 measurements.

In Example 42, the subject matter of Examples 30-41 includes, wherein transmitting further comprises transmitting the at least one image to the remote electronic device via a wired connection.

In Example 43, the subject matter of Examples 30-42 includes, wherein transmitting further comprises transmitting the at least one image to the remote electronic device via a wireless connection over a network.

In Example 44, the subject matter of Examples 30-43 includes, wherein interrogating includes pulsing each of the at least three sources on and off at unique intervals with respect to the remaining ones of the at least three sources.

In Example 45, the subject matter of Examples 30-44 includes, wherein the diode comprises a light-emitting diode (LED).

In Example 46, the subject matter of Examples 30-45 includes, wherein, as part of the interrogating, flooding the lens of the eye with interrogating radiation between 420 nm and 440 nm.

In Example 47, the subject matter of Examples 30-46 includes, wherein the one or more processors are further configured to activate the illuminator for a select time per measurement and, during or immediately subsequent to the select time, activate the detector to obtain at least one image corresponding to the measurement.

In Example 48, the subject matter of Example 47 includes, wherein the select time is from 2 seconds to 30 seconds.

In Example 49, the subject matter of Examples 47-48 includes, wherein the one or more processors are further configured to sequentially perform 2 to 30 measurements.

In Example 50, a method is provided that may include discriminating an autofluorescence response of a target tissue of an eye due to a current level of 2-(2-furoyl)-4(5)-furanyl-1H-imidazole (FFI) in the target tissue, including illuminating the target tissue with excitation radiation having a peak wavelength of 430 nm, the target tissue including a crystalline lens, measuring, as the autofluorescence response of the target tissue due to the current level of FFI, a spectral response of the target tissue, determining a current level of FFI in the target tissue based on at least the spectral response of the target tissue, analyzing a measure of accumulation of FFI, the analyzing including analyzing the current level of FFI in the target tissue and one or more previous levels of FFI in the target tissue, and based on the analyzing, determining a disease state of a patient.

In Example 51, the subject matter of Example 50 wherein the disease state is one or more of a diabetic disease state or an Alzheimer's disease state.

In Example 52, the subject matter of Examples 50-51 wherein the spectral response further comprises an FFI spectral response, and the method further includes discriminating an autofluorescence response of the target tissue due to a current level of all advanced glycation end products (AGEs) in the target tissue, including illuminating the target tissue with excitation radiation having a peak wavelength of 375 nm, the target tissue including a crystalline lens; and measuring, as the autofluorescence response of the target tissue due to the current level of all AGEs in the tissue, a total AGE spectral response of the target tissue.

In Example 53, the subject matter of Examples 50-52, wherein determining further comprises determining, as the current level of FFI, the ratio of the FFI spectral response to the total AGE spectral response of the target tissue.

In Example 54, the subject matter of Examples 50-53, wherein the spectral response of the target tissue includes one or more of a total autofluorescence, a level of fluorescence intensity or a ratio of a level of fluorescence intensity to a level of scattered light.

In Example 55, the subject matter of Examples 50-54, wherein the analyzing includes determining changes in one or more of the total autofluorescence, the level of fluorescence or the scattering spectra associated with one or more of the current level of FFI or changes in the level of FFI over a select time.

In Example 56, the subject matter of Examples 50-55, wherein the analyzing includes comparing the current level of FFI to a baseline level of FFI obtained from the patient in a disease-free condition.

In Example 57, the subject matter of Examples 50-56, wherein the analyzing includes comparing the current level of FFI to one or more baseline levels of FFI obtained from one or more of an age-normed, a gender-normed, or an ethnicity-normed control value.

In Example 58, the subject matter of Examples 50-57 wherein the determining includes determining the presence, concentration, change in concentration, or rate of change in concentration of FFI over a select time.

In Example 59, a device is provided that may include an input to receive a user instruction to perform an action, one or more processors, and a memory storing program instructions accessible by the one or more processors. Responsive to execution of the program instructions, the one or more processors perform the following: discriminate an autofluorescence response of a target tissue of an eye due to a current level of 2-(2-furoyl)-4(5)-furanyl-1H-imidazole (FFI) in the target tissue, including illuminating the target tissue with excitation radiation having a peak wavelength of 430 nm, the target tissue including a crystalline lens; measure, as the autofluorescence response of the target tissue due to the current level of FFI, a spectral response of the target tissue; determine a current level of FFI in the target tissue based on at least the spectral response of the target tissue; analyze a measure of accumulation of FFI, the analyzing including analyzing the current level of FFI in the target tissue and one or more previous levels of FFI in the target tissue; and based on the analyze, determine a disease state of a patient.

In Example 60, the subject matter of Example 59, wherein the disease state is one or more of a diabetic disease state or an Alzheimer's disease state.

In Example 61, the subject matter of Examples 59-60, wherein the spectral response further comprises an FFI spectral response, the one or more processors are further configured to discriminate an autofluorescence response of the target tissue due to a current level of all advanced glycation end products (AGEs) in the target tissue, including illuminate the target tissue with excitation radiation having a peak wavelength of 375 nm, the target tissue including a crystalline lens; and measure, as the autofluorescence response of the target tissue due to the current level of all AGEs in the tissue, a total AGE spectral response of the target tissue.

In Example 62, the subject matter of Examples 59-61, wherein the one or more processors are further configured to, as part of the determine, determine, as the current level of FFI, the ratio of the FFI spectral response to the total AGE spectral response of the target tissue.

In Example 63, the subject matter of Examples 59-62 wherein the spectral response of the target tissue includes one or more of a total autofluorescence, a level of fluorescence intensity or a ratio of a level of fluorescence intensity to a level of scattered light.

In Example 64, the subject matter of Examples 59-63, wherein the one or more processors are further configured to, as part of the analyze, determine changes in one or more of the total autofluorescence, the level of fluorescence or the scattering spectra associated with one or more of the current level of FFI or changes in the level of FFI over a select time.

In Example 65, the subject matter of Examples 59-64 wherein the one or more processors are further configured to, as part of the analyze, compare the current level of FFI to a baseline level of FFI obtained from the patient in a disease-free condition.

In Example 66, a computer program product is provided that includes a non-signal computer readable storage medium comprising computer executable code to: discriminate an autofluorescence response of a target tissue of an eye due to a current level of 2-(2-furoyl)-4(5)-furanyl-1H-imidazole (FFI) in the target tissue, including illuminating the target tissue with excitation radiation having a peak wavelength of 430 nm, the target tissue including a crystalline lens; measure, as the autofluorescence response of the target tissue due to the current level of FFI, a spectral response of the target tissue; determine a current level of FFI in the target tissue based on at least the spectral response of the target tissue; analyze a measure of accumulation of FFI, the analyzing including analyzing the current level of FFI in the target tissue and one or more previous levels of FFI in the target tissue; and based on the analyze, determine a disease state of a patient.

In Example 67, the subject matter of Example 66, wherein the disease state is one or more of a diabetic disease state or an Alzheimer's disease state.

In Example 68, the subject matter of Examples 66-67, wherein the spectral response further comprises an FFI spectral response, the computer program product further comprising computer executable code to: discriminate an autofluorescence response of the target tissue due to a current level of all advanced glycation end products (AGEs) in the target tissue, including illuminate the target tissue with excitation radiation having a peak wavelength of 375 nm, the target tissue including a crystalline lens; and measure, as the autofluorescence response of the target tissue due to the current level of all AGEs in the tissue, a total AGE spectral response of the target tissue.

In Example 69, the subject matter of Examples 66-68, further comprising computer executable code to, as part of the determine, determine, as the current level of FFI, the ratio of the FFI spectral response to the total AGE spectral response of the target tissue.

Example 70 is at least one machine-readable medium including instructions that, when executed by processing circuitry, cause the processing circuitry to perform operations to implement of any of Examples 1-69.

Example 71 is an apparatus comprising means to implement of any of Examples 1-69.

Example 72 is a system to implement of any of Examples 1-69.

Example 73 is a method to implement of any of Examples 1-69.

CLOSING STATEMENTS

In accordance with at least one embodiment herein, to the extent that mobile devices are discussed herein, it should be understood that they can represent a very wide range of devices, applicable to a very wide range of settings. Thus, by way of illustrative and non-restrictive examples, such devices and/or settings can include mobile telephones, tablet computers, and other portable computers such as portable laptop computers.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified.

The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

Although illustrative example embodiments have been described herein with reference to the accompanying figures, it is to be understood that this description is not limiting and that various other changes and modifications may be affected therein by one skilled in the art without departing from the scope or spirit of the disclosure.

The modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming.

The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof.

The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, in the following claims, the phrases "at least A or B", "A and/or B", and "one or more of A and B" (where "A" and "B" represent claim elements), are used to encompass i) A, ii) B and/or iii) both A and B.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A device, comprising:
    an illuminator operable to interrogate at least a lens of an eye, the illuminator comprising at least one light source and a lens positioned with respect to the light source to produce interrogating radiation, wherein the at least one light source is fixed relative to an eye aperture disposed in a housing of the device;
    a detector operable to image the total autofluorescence response of the lens of the eye as viewable through a pupil of the eye, the detector comprising an image sensor;
    a controller operable to control operation of the illuminator and the detector, wherein the controller includes an input to receive an instruction to perform an action, one or more processors, and a memory storing program instructions accessible by the one or more processors, wherein, responsive to execution of the program instructions, the one or more processors perform the following:
        interrogate at least the lens of the eye by activating the illuminator for a select time;
        analyze a plurality of candidate images of the total autofluorescence response of the lens of the eye as viewable through a pupil of the eye based on the interrogation of the at least the lens of the eye, wherein analyzing each image of the plurality of candidate images comprises:
            discerning a median location of a peak wavelength of the at least one image;
            performing an average of an area of the median location of the peak wavelength of the at least one image; and
            determining a total lens autofluorescence index based on the average of the area of the median location of the peak wavelength of the at least one image.

2. The device of claim 1, wherein the at least one light source has a peak wavelength of in a range between 425 nm and 460 nm.

3. The device of claim 1, wherein the light source includes a laser diode or a light-emitting diode (LED).

4. The device of claim 1, wherein the illuminator further comprises a narrow bandpass filter positioned between the at least one light source and the eye aperture.

5. The device of claim 1, further comprising a visible target to facilitate alignment of the eye with the detector.

6. The device of claim 1, further comprising an eyecup disposed on an exterior of the housing about the eye aperture for receiving and stabilizing the eye with respect to the illuminator and the detector.

7. The device of claim 1, wherein the detector further comprises a detector filter disposed between a sensor of the detector and the eye aperture.

8. A method, comprising:
    analyzing a plurality of candidate images of the total autofluorescence response of the lens of the eye as viewable through a pupil of the eye, wherein analyzing each image of the plurality of candidate images comprises:
    analyzing the image to determine a symmetry value and a definition value of a pupil spot of a pupil;
    analyzing the symmetry value and the definition value of the pupil to confirm at least one image;
    discerning a median location of a peak wavelength of the at least one image;
    performing an average of an area of the median location of the peak wavelength of the at least one image; and
    determining a total lens autofluorescence index based on the average of the area of the median location of the peak wavelength of the at least one image.

9. The method of claim 8, wherein determining the total lens autofluorescence index comprises determining a total lens autofluorescence value based on the plurality of images normalized by the area of the median location to determine a normalized total lens autofluorescence value.

10. The method of claim 8, wherein determining the total lens autofluorescence index further comprises normalizing the normalized total lens autofluorescence value with a calibration value.

11. The method of claim 10, wherein the calibration value comprises a total lens calibration autofluorescence index.

12. The method of claim 11, wherein determining the total lens calibration autofluorescence index comprises determining a total lens calibration autofluorescence value based on at least one calibration image normalized by the area of the calibration median location to determine the total lens calibration autofluorescence value.

13. The method of claim 8, wherein the total lens calibration autofluorescence index is used to determine a disease state of the patient.

14. A computer program product comprising a non-transitory computer readable storage medium comprising computer executable code to:
    interrogate at least a lens of an eye by activating an illuminator for a select time, the illuminator comprising an array of at least three sources that are spaced about to a central point, each of the at least three sources fixed relative to an eye aperture disposed in a housing of the device, each of the at least three sources including a diode and a lens positioned with respect to the diode to produce interrogating radiation, each of the at least three sources for simultaneously interrogating corresponding at least three unique retinal locations of the eye;

obtain at least one candidate image of the total autofluorescence response of the lens of the eye as viewable through a pupil of the eye at a detector, the detector comprising an image sensor;

analyze the at least one candidate image of the total autofluorescence response of the lens of the eye as viewable through a pupil of the eye to determine a total lens autofluorescence index, wherein analyzing the at least one candidate image comprises:
 analyze the at least one candidate image to determine a symmetry value and a definition value of a pupil spot of a pupil;
 analyze the symmetry value and the definition value of the pupil to confirm at least one image;
 discern a median location of a peak wavelength of the at least one image;
 perform an average of an area of the median location of the peak wavelength of the at least one image; and
 determine the total lens autofluorescence index based on the average of the area of the median location of the peak wavelength of the at least one image.

15. The computer program product of claim 14, further comprising computer executable code to, as part of the determine the total lens autofluorescence index, determine a total lens autofluorescence value based on the plurality of images normalized by the area of the median location to determine a normalized total lens autofluorescence value.

16. The computer program product of claim 15, further comprising computer executable code to, as part of the determine the total lens autofluorescence index, normalize the normalized total lens autofluorescence value with a calibration value.

* * * * *